United States Patent [19]

Lignell et al.

[11] Patent Number: 6,054,491

[45] Date of Patent: Apr. 25, 2000

[54] AGENT FOR INCREASING THE PRODUCTION OF/IN BREEDING AND PRODUCTION MAMMALS

[75] Inventors: Åke Lignell, Värmdö; Johan Inborr, Lidköping, both of Sweden

[73] Assignee: Astacarotene AB, Gustavsberg, Sweden

[21] Appl. No.: 09/147,046

[22] PCT Filed: Mar. 21, 1997

[86] PCT No.: PCT/SE97/00488

§ 371 Date: Sep. 25, 1998

§ 102(e) Date: Sep. 25, 1998

[87] PCT Pub. No.: WO97/35491

PCT Pub. Date: Oct. 2, 1997

[30] Foreign Application Priority Data

Mar. 27, 1996 [SE] Sweden .................................. 9601197

[51] Int. Cl.[7] .................................. A23K 1/16; A23K 1/18
[52] U.S. Cl. .............................................................. 514/725
[58] Field of Search .............................................. 514/725

[56] References Cited

U.S. PATENT DOCUMENTS 5,744,502  4/1998  Lignell et al. ............................ 514/725

FOREIGN PATENT DOCUMENTS 06153818  6/1994  Japan .

Primary Examiner—Phyllis G. Spivack
Attorney, Agent, or Firm—Bacon & Thomas

[57] ABSTRACT

A method of increasing the production of/in breeding and production mammals by administering an agent which consists of at least one type of xanthophylles, preferably astaxanthin, in the feed to animals, is disclosed.

5 Claims, No Drawings

AGENT FOR INCREASING THE PRODUCTION OF/IN BREEDING AND PRODUCTION MAMMALS

This application is a 371 of PCT/SE97/00488 filed Mar. 21, 1997.

The present invention relates to an agent for increasing the production of/in breeding and production mammals, to a method of increasing the production with said agent and the use of said agent. The agent consists of at least one type of xanthophylles, preferably naturally produced astaxanthin. It is administered in the feed to breeding and production animals to obtain increased production thereof.

BACKGROUND

In the food, livestock, breeding animal and domestic animal industry the production of/in breeding and production animals is of great importance to the economy. Hence, there is a demand for agents that increase the productivity by for example improved fertility, more progeny born alive (especially pig, cow and sheep), lower mortality after birth, increased growth during the sucking period, higher milk production, shorter recovery period between weaning and new heat, and generally improved state of health due to strengthened immune defence.

The present invention now provides such an agent, which consists of at least one type of xanthophylles, preferably naturally produced astaxanthin Astaxanthin belongs to the xanthophylles, which is a large group of carotenoids containing oxygen in the molecule in addition to carbon and hydrogen. The carotenoids are produced de novo by plants, fungi and some bacteria.

Xanthophylles have since long been used in the feed for laying hens and in some parts of the world in the feed for broilers, but not in the feed for breeding or production mammals. The purpose has solely been to pigment the product, the yolk or fat and skin tissue, to satisfy the demands of the consumers. As sources for pigment both naturally produced xanthophylles and synthetically produced ones have been used (Hencken H., 1992, Poultry Science 71:711–717, Karunajeewa H. & A. Hoffman, 1992, Arch für Geflugeikunde 56(3):109–112).

Thus, it has not previously been known that xanthophylles, and among them astaxanthin, have the ability to increase the production of/in breeding and production mammals.

The reason for the improved productivity when astaxanthin enriched feed is used according to the present invention is not known, but it can be assumed to be due to the antioxidative properties of astaxanthin, and hence the ability to scavenge so-called free radicals. The other xanthophylles do also have antioxidative properties. However, in biological tests astaxanthin has been shown to possess clearly the best antioxidative properties compared to other carotenoids (Miki W., 1991, Pure and Appl Chem 63 (1): 141–146).

DESCRIPTION OF THE INVENTION

The present invention thus provides an agent for increasing the production of/in breeding and production mammals, which agent consists of at least one type of xanthophylles.

Examples of breeding and production mammals are pigs, cattle, sheep, horses, dogs etc.

In a preferred embodiment the type of xanthophylles is astaxanthin. In a particularly preferred embodiment the astaxanthin exists in a form in which it is esterified with fatty acids. The last mentioned form of astaxanthin may be produced by cultivation of the alga *Haematococcus sp.*

The agent according to the invention may consist of a mixture of different types of xanthophylles or different forms of the same xanthophyll, such as a mixture of synthesized astaxanthin and naturally produced astaxanthin.

The present invention further provides a method of increasing the production of/in breeding and production mammals, in which an agent, which consists of at least one type of xanthophylles, is administered in the feed to said mammals.

In an embodiment of said method the type of xanthophyll is preferably astaxanthin. In a preferred embodiment of said method according to the invention, astaxanthin which exists in the form esterified with fatty acids, is administered. The amount of agent administered is suitably in the range of 1 to 50 mg agent per kg feed.

The present invention further comprises the use of an agent which consists of at least one type of xanthopylles for increasing the production of/in breeding and production mammals by administering said agent in the feed to said mammals.

Also in this aspect of the invention the preferred type of xanthophyll is astaxanthin, which in a particularly preferred embodiment exists in a form esterified with fatty acids.

DESCRIPTION OF EXPERIMENTS AND PREPARATION OF THE AGENT

The agent used in the experiments was the xanthophyll astaxanthin which was produced via algae, and the mammals used were pigs.

Astaxanthin from other sources, and other xanthophylles as well, are expected to be similarly useful for the purposes of the invention. An advantage of using astaxanthin from algae is, however, that the astaxanthin exists in a form esterified with fatty acids (Renström B. et al, 1981, Phytochem 20(11) :2561–2564), which esterified astaxanthin thereby is more stable during handling and storage than free astaxanthin.

The naturally produced astaxanthin can be obtained also from fungi and crustaceans, in addition to from algae. The astaxanthin used in the present test was produced via culturing of the algae *Haematococcus sp.* in the way described below.

*Haematococcus sp.* is a single-cell green algae belonging to the order Vovocales, family Chlamydomonadaceae. The reproduction takes normally place through asexual cell-division, but isogam sexual reproduction occures sporadically. When the alga is batch-cultivated it grows in the form of flagella-equipped so-called macrozoides. When the nutrient content of the medium decreases and becomes limiting for continuing growth, the cells lose the flagella and go into a palmella stage and form thereafter so-called haematocystes. They are characterized by a strong cell wall which encloses the cell, which in turn is rich in fatty vacuoles in which astaxanthin is accumulated. The haematocyst is a resting stage for the alga by which it can survive periods of dryness etc.

For the production a species or strain of *Haematococcus sp.* which grows fast and produces high titres of astaxanthin is suitably selected. A number of different species and strains of Haematococcus are available via so-called culture collections, and there is also the possibility of isolating a suitable strain from wild-growing populations. A suitable species is *H. pluvialis* which is available from NIVA, Norway.

Stock cultures of the algae are kept in axenic culture in a medium suitable therefore, see Table 1. The temperature should be approximately +25° C. and the light intensity about 50 $\mu Em^{-2}S^{-1}$.

TABLE 1

Composition of growth medium for Haematococcus sp.

| | |
|---|---|
| $Ca(NO_3)_2 \times 4H_2O$ | 85 μM |
| $KH_2PO_4$ | 91 μM |
| $MgSO_4 \times 7H_2O$ | 203 μM |
| $NaHCO_3$ | 189 μM |
| $EDTA\ Na_2$ | 7 μM |
| EDTA FeNa | 6 μM |
| $H_3BO_3$ | 40 μM |
| $MnCl_2 \times 4H_2O$ | 7 μM |
| $(NH_4)_6Mo_7O_{24} \times 4H_2O$ | 0.8 μM |
| Vitamin $B_{12}$ | 10 μg/l |
| Vitamin $B_1$ | 10 μg/l |
| Biotin | 10 μg/l |
| $NaNO_3$ | 940 μM |
| $NaH_2PO_4 \times 12H_2O$ | 100 μM |

Inoculation material is taken from the stock cultures for the production culture. The cell density at inoculation is >5000 cells/ml and the culture is reinoculated to a larger volume as the cell density reaches approximately 200 000 cells/ml, which will take approximately five days. At cultivation of the algal material the temperature is kept around +25° C. and the light intensity should be approximately 100 $\mu Em^{-2}S^{-1}$. The same composition of the medium is used as for the stock cultures. The cultures are agitated with compressed air which is enriched with 1–5% $CO_2$. Alternatively, $CO_2$ may be added separately in such an amount that the pH value of the medium is kept between 6.5–8.5.

When the volume of the algal culture reaches approximately 100 liters it is used for inoculation of a production unit, which consists of a device wherein the algal cells can be exposed to light also when the culture volume may amount to 2–100 $m^3$. Such a device may be designed as a shallow pond, a construction of transparent tubes, panels orientated against a source of light or alternatively, as in the example, a tank equipped with submerged lighting in the form of fluorescent lamps.

The production vessel is inoculated with a cell density of >5000 cells/ml and the medium is enriched with nutrient salts in accordance with Table 1. The temperature is kept at approximately +25° C. and the light intensity should be 100 $\mu Em^{-2}S^{-1}$. The culture is agitated with the aid of compressed air. Carbon dioxide is added to the culture so that the pH value will be between 6.5–8.5. When the nutrition in the medium begins to cease the algal cells turn over to the palmella stage and begin to synthesize astaxanthin. In this connection the light intensity is suitably increased to approximately 250 $\mu Em^{-2}S^{-1}$, the temperature to +30° C. and NaCl is added to the medium so that a salt content of 0.1–0.3% is obtained. These changes are made in order to accelerate the production of astaxanthin. In 10–20 days the cells have produced haematocysts and the cell density has increased to $5-10 \times 10^5$ cells/ml.

The cells are separated from the medium via sedimentation or via centrifugation. The harvested algal cells in the form of a paste are then passed through a homogenizer in order to brake the cell walls. The paste consisting of cells having broken cell walls may then be taken care of in two alternative ways. The paste may either be dried so that a dry powder is obtained. The drying should be done as leniently as possible so that the astaxanthin will not be degraded. An alternative to drying the paste is to extract the pigment from the paste. Since astaxanthin is highly hydrofobic the extraction can be made with a suitable oil, e.g. soy oil.

The amount of astaxanthin in the feed shuould preferrably been in the range of 1–50 mg astaxanthin/kg feed, and in the following experiments 5 mg astaxanthin/kg feed was used.

EXPERIMENT

The present experiment was conducted to investigate the effect of supplementing the sow diet with astaxanthin in 21 day period before parturition and during lactation on the growth rate of piglets weaned onto diets with or without astaxanthin supplementation.

MATERIALS AND METHODS

Experimental Design

A commercial sow feed was supplemented with (5 mg/kg) and without natural astaxanthin (*Haematococcus pluvialis*) and fed to pregnant sows to give two is experimental treatments.

A total of 739 sows of parity two and above were divided into two experimental groups on the bases of parity and age. The sows were fed their respective experimental feeds from 35 days prior to farrowing, during lactation and until 21 days post weaning.

The number of born and stillborn piglets, and the number of piglets that died before weaning were recorded. In addition, the litter weight on day 21 after birth and the number of days between weaning and remating was recorded (Table 2). These measurements were also carried out during the subsequent parity (Table 3).

TABLE 2

Effect of natural astaxanthin (*Haematococcus pluvialis*) supplementation (5 mg/kg) of sow feed on sow performance.

| | Treatment | | |
|---|---|---|---|
| | Control | Astaxanthin 5 mg/kg | Significance (P=) |
| Number of piglets born | 10.43 | 10.65 | 0.139 |
| Percentage stillborn | 8.76 | 8.08 | 0.919 |
| Number of stillborn/litter | 0.90 | 0.70 | 0.479 |
| Litter weight at 21 days of age, kg | 49.50 | 52.60 | 0.001* |

*The effect is statistically significant (P < 0.05)

TABLE 3

Performance of sows having received natural astaxanthin (*Haematococcus pluvialis*) during the preceding lactation period and 21 days post weaning.

| Parity | Astaxanthin | FR (%) | WRMI, days | B.A. | S.B.P. (%) |
|---|---|---|---|---|---|
| 2 | − | 93 | 10.30 | 10.7 | 7.4 |
|   | + | 85 | 7.40 | 10.9 | 7.5 |
| 3 | − | 86 | 10.00 | 11.0 | 5.8 |
|   | + | 83 | 8.20 | 9.4 | 6.1 |
| 4 | − | 81 | 11.0 | 10.3 | 11.1 |
|   | + | 80 | 7.30 | 10.4 | 9.4 |
| 5 | − | 77 | 9.20 | 10.5 | 14.0 |
|   | + | 73 | 7.70 | 9.8 | 14.0 |
| Significance | | | | | |
| Astaxanthin (A) | | 0.211 | 0.004* | 0.461 | 0.786 |
| Parity(P) | | 0.045* | 0.366 | 0.119 | 0.001* |
| A*P | | 0.927 | 0.740 | 0.769 | 0.906 |

*The effect is statistically significant (P < 0.5)
FR = Farrowing rate
WRMI = Weaning to remating interval
BA = Number of pigs born alive
SBP = Stillborn percentage From the results presented above it can be concluded that naturally produced astaxanthin improves the performance of sows.

What is claimed is:

1. A method of increasing the production of/in breeding and production mammals, c h a r a c t e r i z e d in that an agent which consists of at least one type of xanthophylles is administered in the feed to said mammals.

2. The method according to claim 1, wherein the type of xanthophyll is astaxanthin.

3. The method according to claim 2, wherein the astaxanthin exists in a form esterified with fatty acids.

4. The method according to claim 2, wherein the amount of agent administered is in the range of 1 to 50 mg agent per kilogram feed.

5. The method according to claim 3, wherein the amount of agent administered is in the range of 1 to 50 mg agent per kilogram feed.

* * * * *